United States Patent [19]

Morrison, Jr.

[11] 4,040,426
[45] Aug. 9, 1977

[54] ELECTROSURGICAL METHOD AND APPARATUS FOR INITIATING AN ELECTRICAL DISCHARGE IN AN INERT GAS FLOW

[75] Inventor: Charles F. Morrison, Jr., Boulder, Colo.

[73] Assignee: Valleylab, Inc., Boulder, Colo.

[21] Appl. No.: 649,682

[22] Filed: Jan. 16, 1976

[51] Int. Cl.$^2$ .............................................. A61B 17/36
[52] U.S. Cl. ............................ 128/303.17; 219/121 P
[58] Field of Search ........... 128/303.1, 303.17, 303.14, 128/303.13, DIG. 22; 219/121 P, 75

[56] References Cited

U.S. PATENT DOCUMENTS

| 2,376,265 | 5/1945 | Meredith | 219/75 |
| 3,204,076 | 8/1965 | Browning | 219/121 P X |
| 3,434,476 | 3/1969 | Shaw et al. | 128/303.1 |
| 3,612,807 | 10/1971 | Liefkens et al. | 219/121 P |
| 3,832,513 | 8/1974 | Klasson | 219/121 P X |

OTHER PUBLICATIONS

"RF and Laser Combine to Produce High-Energy Beam", *Machine Design*, Nov. 27, 1975.

*Primary Examiner*—Robert W. Michell
*Assistant Examiner*—Michael H. Thaler
*Attorney, Agent, or Firm*—Gerald J. Ferguson, Jr.; Joseph J. Baker

[57] ABSTRACT

A method and apparatus for initiating an electrical discharge in a formation of flowing inert gas disposed adjacent the end of an active electrode by generating charged particles in the vicinity of said inert gas formation. The charged particles are generated by an auxiliary electrical discharge produced between the active electrode and a surrounding tube, which is not connected to any external source of biasing potential. Electrostatic charge is generated on the tube as the inert gas flows thereby. This charge bleeds off the tube through inwardly pointed tips on the tube, which act as discharge points. The charge then passes to the active electrode via the auxiliary discharge through the gas.

21 Claims, 4 Drawing Figures

ELECTROSURGICAL METHOD AND APPARATUS FOR INITIATING AN ELECTRICAL DISCHARGE IN AN INERT GAS FLOW

RELATED APPLICATIONS

This application is related to a first U.S. Pat Ser. Application No. 649,725 filed on Jan. 16, 1976 by Charles F. Morrison, Jr., Frank W. Harris, and Michael C. Patzer, entitled "Electrosurgical Method and Apparatus for Establishing an Electrical Discharge in an Inert Gas Flow" and a second U.S. Ser. Pat. Application No. 649,683 filed on Jan. 16, 1976 by Charles F. Morrison, Jr. and Benson C. Weaver, entitled "Electrosurgical Method and Apparatus for Initiating an Electrical Discharge in an Inert Gas Flow", all the foregoing applications being assigned to the same assignee.

BACKGROUND OF THE INVENTION

This invention relates to the initiation of electrical discharges and in particular to the initiation of such discharges in inert gas flows.

In the first of the above-mentioned related patent applications, there is disclosed a method and apparatus for establishing an electrical discharge from an electrode by forming a column of inert gas adjacent the electrode whereby the discharge is both long and directed. There is also disclosed an electrosurgical method and apparatus for coagulating by fulguration where a long electrical discharge is established either through a diffuse blanket of inert gas or a well defined column of the gas. Since the discharge is long, any tendency for the electrode to contact the surface being treated is substantially lessened whereby undesirable sticking of coagulated tissue to the electrode in electrosurgical applications is practically eliminated. However, there is some difficulty in initiating this long electrical discharge and thus, it is necessary to touch the electrode down on or very near to the tissue being coagulated. This can also result in adhesion of tissue to the hot electrode where the tissue can be ripped away when the instrument is removed from the site thereby causing surgical complications. Further, the adhered tissue tends to foul the electrode such that it must be scraped clean before the surgical procedure can continue.

In the second of the above-mentioned related patent applications, there is disclosed a method and apparatus for initiating the electrical discharge where an auxilliary source of charged particles is employed. In one embodiment an auxilliary electrical discharge in electrical series with the active electrode generates the charged particles. This arrangement is advantageous in that no external means are needed to generate the charged particles. However, all power from the gnerator to the patient must pass through the auxilliary gap and thus, there is some undesirable power loss.

SUMMARY OF THE INVENTION

With this invention, the above difficulties can be eliminated. Further, as will be brought out in detail hereinafter, extension of the invention to non-surgical applications such as thermal-inert-gas welding is also advantageous and desirable.

A primary object of this invention is the provision of a method and apparatus for initiating a long electrical discharge in a formation of inert gas with little, if any power loss and without the need for external charged particle generating means.

A further object of this invention is the provision of an electrosurgical method and apparatus for coagulating by fulguration where the electrical discharge is initiated and established either through a diffuse blanket of inert gas or a well defined column of the gas.

These and other objects of the invention will become apparent from a reading of the following specification and claims taken together with the drawing.

DETAILED DESCRIPTION OF THE PREFERRED EMBODIMENTS OF THE INVENTION

Figure 1:
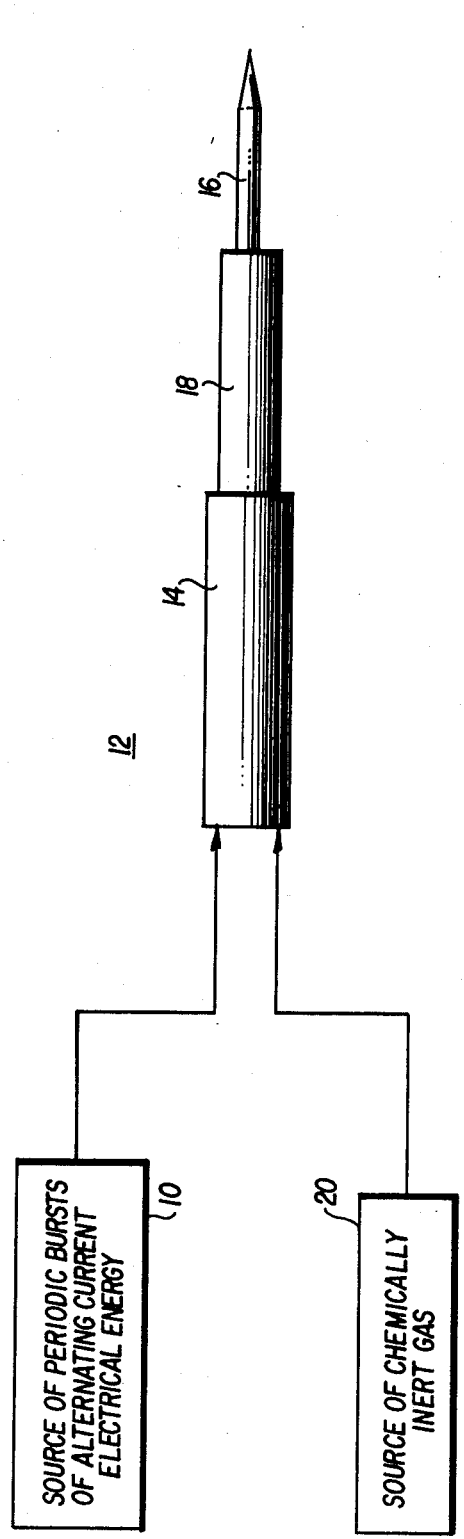
FIG. 1 is an illustrative schematic diagram of apparatus in accordance with the invention.

Referring to the figures of the drawing where like reference numerals refer to like parts and, in particular, referring to FIG. 1, there is shown a source 10 of electrical energy which may be continuous or preferably discontinuous such as periodic bursts of electrical energy as illustrated in FIG. 7 of U.S. Pat. No. 3,699,967 granted to Robert K. Anderson. This energy is typically in the high frequency range — that is, about 200 kHz or higher. The waveform has a high crest factor — that is, typically about 5–10 where the crest factor of periodic function is the ratio of its crest (peak, maximum) value to its root-mean-square value. The bursts may occur at a repetition rate of 15,000 to 50,000 bursts per second while the duration of each burst may consist of 1 to 5 cycles of the high frequency energy, it being understood that none of the foregoing values is critical. Such waveforms are well known for use as coagulating waveforms in electrosurgery. It should be understood that source 10 may also generate waveforms of other types such as those used in thermal-inert-gas (TIG) welding.

Source 10 may be connected to an electrosurgical instrument or a welding instrument generally indicated at 12. Instrument 12 basically comprises a support member 14, which may function as a handle. Member 14 supports an active electrode 16, which may be directly supported by member 14 or indirectly supported thereby via an intermediate member 18, although intermediate member 18 does not necessarily also have to be employed as a support member, as will be described in more detail hereinafter. Source 10 may be electrically connected in a conventional manner to electrode 16 by appropriate connections (not shown) internal to members 14 and 18.

A source 20 of gas is also connected to instrument 12 and, as will be described in more detail hereinafter, the gas is employed to support an electrical discharge used for tissue coagulation and the like. The gas should be inert in the sense that it is not combustible by the electrical discharge nor will it support combustion of the electrode 16. It may, for example, be selected from the group consisting of nitrogen and the noble gases and mixtures thereof. Helium has been found to be particularly advantageous as discussed in the first of the beforementioned patent applications.

Figure 2:
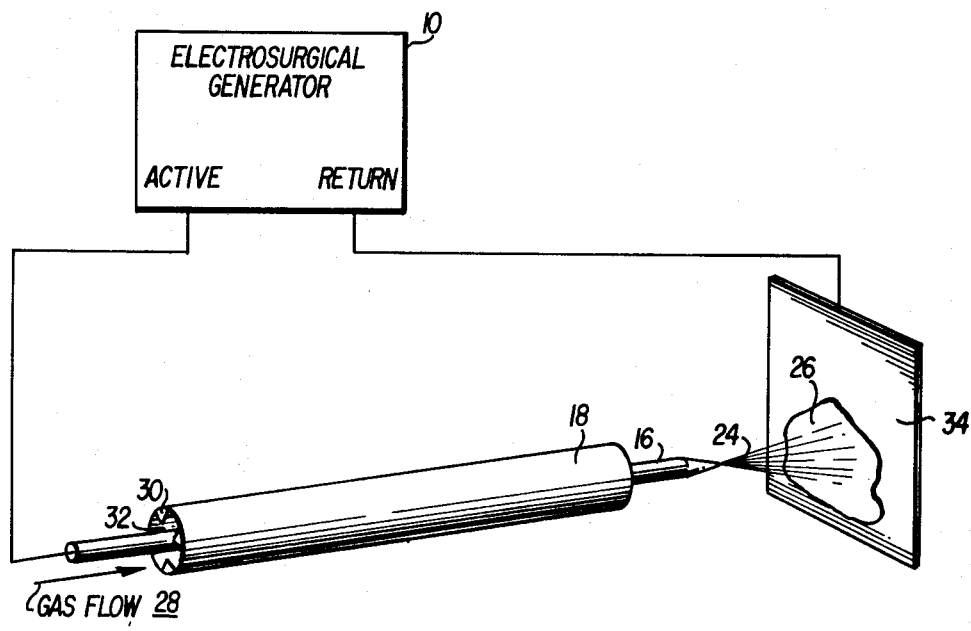
FIG. 2 is a diagrammatic, perspective view of illustrative apparatus in accordance with the invention and in particular, of illustrative means for generating an auxiliary electrical discharge.
Figure 3:
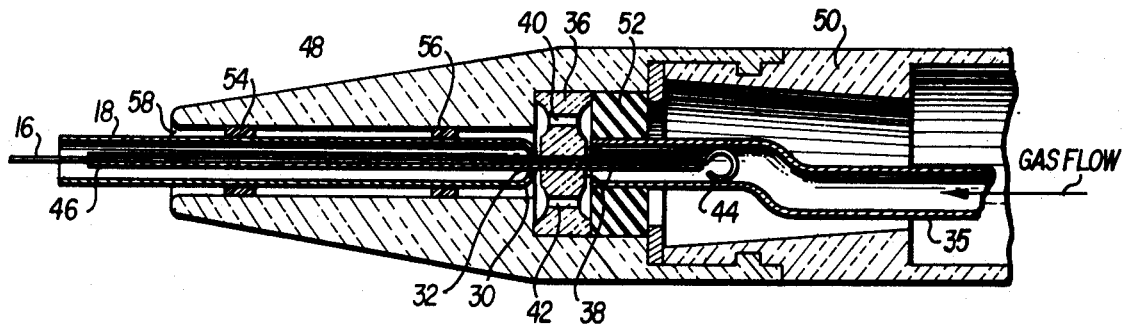
FIG. 3 is a cross-sectional view of an illustrative electrode structure in accordance with the invention.

In FIGS. 2 and 3 there are shown electrode structures generally corresponding to that shown in FIG. 1. Intermediate member 18 comprises a hollow tube disposed about and surrounding electrode 16 whereby an annular passageway is provided through which the gas from source 20 flows. As the gas flows out of tube 18 an outwardly extending column of flowing inert gas is formed adjacent the tip or end of electrode 16 to thereby facilitate the establishment and maintenance of a highly directive discharge 24 to a surface 26 such as body tissue or the like, although in this application the surface 26 may also be metal or the like as in welding operations or the like. The active electrode is electrically conductive and typically may be made from tungsten, stainless steel, etc., as is the tube 18. The radial distance between the forward end of electrode 16 and tube 18 may typically be about 30 mils while the diameter of electrode 16 is typically about 12-15 mils, it being understood that none of the foregoing values are critical to the desired formation of a column of gas.

The outwardly extending column of inert gas is well defined and produces a very long electrical discharge. This discharge is four to six times the length of that generated under the same conditions without the gas. The discharge is straight down the gas column. The directivity of the discharge is such that it can be directed to the bottom of a fissure or crevice without deflecting to the sides thereof.

The directivity and length of the discharge is very disirable; however, there is some difficulty in initiating the discharge and thus, it is necessary to touch the electrode 16 down or very near to the surface 26. This can result in adhesion of tissue to the hot electrode which can cause the tissue to be ripped away when the instrument is removed from surface 26, thereby causing surgical complications. Further, the adhered tissue tends to foul the electrode such that it must be scraped clean before the surgical procedure can continue. To avoid these problems, discharge initiating means generally indicated at 28 are provided. In particular, means 28 preferably comprises a tube 18 and a plurality of pointed projections or tips 30 which inwardly extend from tube 18. An auxiliary electrical discharge is generated between tips 30 and a portion of the active electrode 16, the portion being indicated at 32 where portion 32 is spaced from the tip or forward end of active electrode 16. The location of portion 32 with respect to the tip of electrode 16 is not critical and it need only be removed from the tip to the extent necessary to maintain gas flow integrity. Typically the distance between tips 30 and portion 32 is about 10-20 mils although these values are not critical. As will be explained in more detail hereinafter, the auxiliary electrical discharge is generated by the inert gas flowing by tube 18.

It is thought that the charged particles generated in the auxiliary electrical discharge are swept by the inert gas through tube 18 to the region in front of active electrode 16 whereby an electrical discharge is initiated in the inert gas in front of the electrode assuming an appropriate electrical potential such as that produced by source 10 is on active electrode 16 and assuming active electrode 16 is in the electric field of an appropriate return electrode, such as that indicated at 34 in FIG. 2. The discharge may also be solely due to the electric field associated with the auxiliary discharge or due to both the particles and the electric field, In electrosurgical applications the return electrode would in effect be the patient's body (surface 26) which is in electrical contact with return electrode 34, which preferably has a large area. In welding applications, the return electrode would correspond to the workpiece (surface 26) to be welded. When active electrode 16 is substantially removed from surface 26, but still in the field of the return electrode, the electrical discharge initiated by the auxiliary electrical discharge is a tiny hair line of corona discharge which extends a substantial distance from the active electrode due to the presence of the gas. As active electrode 16 is brought closer to surface 26, the electrical discharge becomes heavy and luminous. Typically, the discharge necessary to effect coagulation by fulguration occurs when the active electrode is within about one-half inch of the tissue and hence, no tissue will undesirably adhere to the electrode. The foregoing theory of operation may not be perfectly correct; in any event, there is no intention to be limited thereby.

The gas flow through tube 18 generates electrostatic charges between active electrode 16 and tube 18. When an RF voltage or the like is applied to the active electrode, the electrostatic charges bleed off of the tube to the electrode through tips 30, which act as discharge points, and thence via the auxiliary electrical discharge through the gas. This discharge than provides part of the necessary corona starting conditions. Bringing the tip into the field of the return electrode provides the remainder. With the tiny corona discharge playing on the flesh, the heavy, luminous discharge will jump only when the distance to the flesh is less than a critical value. Once this discharge has started, it can be drawn to greater than the starting length. When drawn too far, the heavier discharge extinguishes, leaving the corona.

From the foregoing it can be appreciated that tube 18 is not connected to any source of external biasing potential. As stated above, the electrostatic charge needed for the auxiliary discharge is generated on the tube by the gas flowing thereby. Hence, this is a very important feature of the invention in that the need for additional apparatus to generate the auxiliary discharge is eliminated. Another important feature of the invention is that little, if any, of the power from electrical power source 10 is absorbed in the auxiliary discharge. This is in contradistinction to the arrangement disclosed in the aforementioned related patent application entitled "Electrosurgical Method and Apparatus for Initiating an Electrical Discharge in an Inert Gas Flow" where the auxiliary discharge is in electrical series with the active electrode. Thus, all power from source 10 to the patient must pass through the auxiliary gap. As stated above, this is not necessary in accordance with the present invention.

Reference should now be made to FIG. 3 where there is shown an electrode structure embodying the arrangement illustrated in FIG. 2. A brass tube 35, which may have an outside diameter of about 93 mils is connected to the active terminal of generator 10. The gas from source 20 flows through tube 35. The gas flows from the tube via channel 38 through a tube support member 36 having openings 40 and 42. Tube support member 36 may be gas porous, if desired. The gas flows through the gap between tips 30 and portion 32 and down tube 18, which may comprise a metallic No. 12 hypodermic tube. Tips 30 are as shown in FIG. 2.

Electrode 16 may comprise a 12 mil diameter tungsten wire having a bent circular portion 44 at the end thereof which engages the inner surface of tube 35.

Disposed about electrode 16 may be a metallic No. 21 hypordermic tube 46. The distance between the points of tips 30 and portion 32 of tube 46 corresponds to the gap across which the auxiliary electrical discharge is formed and through which the gas from member 36 flows.

Tube 46 and electrode 16 are supported by member 36 where member 36 is disposed in a cavity in a nose cap 48, which is made of an electrically insulative material, as is intermediate member 50. A gas seal plug 52 is employed to prevent gas flow back up around tube 35. Plastic spacers 54 and 56 mount tube 18 within an opening 58, which extends through nose cap 48. It is to be understood where values have been given for certain parameters in the foregoing description, this has been done for purposes of illustration only.

In operation, gas flows through tube 18 to electrostatically charge the tube. When the RF voltage is applied to the electrode 16, the charge bleeds from tips 30 via the auxiliary discharge through the gas to the electrode. Thus, an electrical discharge can be initiated from active electrode 16 at a substantial distance from surface 26 with little, if any power loss in the auxiliary discharge and without the need for external means to initiate the discharge.

Figure 4:
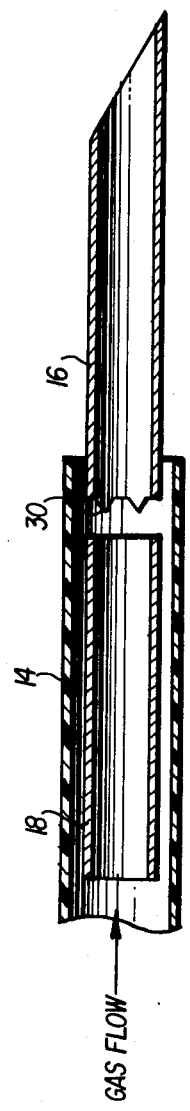
FIG. 4 is a cross-sectional view of a further electrode structure in accordance with the invention.

Referring to FIG. 4, it should be understood that tube 18 need not concentrically disposed about electrode 16 where the parallel embodiment is shown in FIGS. 2 and 3. Rather, tube 18 may also be connected in series with the electrode. Further, electrode 16 may be tubular as shown in FIG. 4. Tube 18 may be collinearly and coaxially disposed with respect to electrode 16. In this embodiment, the tube 18 would preferably, but not necessarily, have about the same internal diameter as that of tubular electrode 16 where the gas would successively flow through, and also possibly around, both of the tubes. Tube 18 would be slightly spaced from electrode 16 and the pointed projections 30 would preferably, but not necessarily, extend straight out from active electrode 16 toward tube 18 rather than be bent where the bent projection arrangement is shown in FIGS. 2 and 3. Electrode 16 need not be tubular in this serial embodiment. If not tubular, the projections 30 would more than likely be bent toward the tube. The distance between the projections or tips 30 and tube 18 in this serial embodiment would typically be about 10-20 mils although these values are not critical. The serial embodiment is advantageous in that the tube 18 can be disposed within support member or handle 14 whereby a particularly compact arrangement can be implemented. Also with respect to the projection 30, it should be appreciated that in both the serial and parallel embodiments, they may be disposed on either the tube 18 or electrode 16 or on both.

What is claimed is:

1. Apparatus for establishing an electrical discharge to an object comprising
a support;
a source of electrical energy;
an active electrode connected to said source of electrical energy and being supported by said support and outwardly extending therefrom;
a source of inert gas;
gas flow directing means connected to said source of inert gas for directing the gas past said electrode to thereby facilitate the establishment of a primary electrical discharge in the gas disposed adjacent the end of the electrode and extending outwardly therefrom;
discharge initiating means disposed adjacent to said electrode for initiating said electrical discharge in said gas formed adjacent the end of the electrode, said discharge initiating means including said active electrode and a second electrode having a small gap therebetween, across which an auxiliary discharge initiates said primary electrical discharge;
said second electrode being electrically isolated from any source of biasing potential and being so disposed in the gas flow established by said gas flow directing means that said gas generates electrostatic charge on said second electrode, which is discharged through said gas to said active electrode to thereby establish said auxiliary electrical discharge; and
means for returning said electrical energy from said object to said source of electrical energy.

2. Apparatus as in claim 1 where said second electrode is an electrically conductive tube disposed about and surrounding said active electrode.

3. Apparatus as in claim 2 where said second electrode includes at least one inwardly directed, pointed projection extending from said tube whereby said auxiliary discharge occurs between said pointed projection and said active electrode.

4. Apparatus as in claim 1 including an electrically conductive tube connected to said source of inert gas, through which said gas flows, said tube also being connected to said source of electrical energy at one end thereof and to said active electrode at the other end thereof.

5. Apparatus as in claim 1 where said second electrode is an electrically conductive tube which is substantially collinearly disposed with respect to said active electrode so that said gas first flows by said tube to generate said electrostatic charge thereon and then it flows past said active electrode.

6. Apparatus as in claim 5 where said active electrode is tubular.

7. Apparatus as in claim 6 where the tubular active electrode includes at least one projection extending therefrom whereby said auxiliary discharge occurs between said pointed projection and said active electrode.

8. Apparatus as in claim 1 where said discharge initiating means includes at least one pointed projection extending from at least said second electrode.

9. Apparatus as in claim 1 where said discharge initiating means includes at least one pointed projection extending from at least said active electrode.

10. An instrument comprising
a support;
an active electrode supported by said support and outwardly extending therefrom;
gas flow directing means adapted for the directing of gas past said electrode to provide gas adjacent the end of the electrode and extending outwardly therefrom; and
discharge initiating means disposed adjacent to said electrode adapted for the initiation of a primary electrical discharge in said gas formed adjacent the end of the electrode, said discharge initiating means including said active electrode and a second electrode having a small gap therebetween, across which an auxiliary discharge initiates said primary electrical discharge;

said second elctrode being electrically isolated from any source of biasing potential and being so disposed in the gas flow established by said gas flow directing means that said gas generates electrostatic charge on said second electrode, which is discharged through said gas to said active electrode to thereby establish said auxiliary electrical discharge.

11. An instrument as in claim 10 where said second electrode is an electrically conductive tube disposed about and surrounding said active electrode.

12. An instrument as in claim 11 where said second electrode includes at least one inwardly directed, pointed projection extending from said tube whereby said auxiliary discharge occurs between said pointed projection and said active electrode.

13. An instrument as in claim 10 where said second electrode is an electrically conductive tube which is substantially collinearly disposed with respect to said active electrode so that said gas first flows by said tube to generate said electrostatic charge thereon and then it flows past said active electrode.

14. An instrument as in claim 13 where said active electrode is tubular.

15. An instrument as in claim 14 where the tubular second electrode includes at least one projection extending therefrom whereby said auxiliary discharge occurs between said pointed projection and said active electrode.

16. An instrument as in claim 10 where said discharge initiating means includes at least one pointed projection extending from at least said second electrode.

17. An instrument as in claim 10 where said discharge initiating means includes at least one pointed projection extending from at least said active electrode.

18. A method of using an instrument comprising a support; an active electrode supported by said support and outwardly extending therefrom; gas flow directing means adapted for the directing of gas past said electrode to provide gas adjacent the end of the electrode and extending outwardly therefrom; discharge initiating means disposed adjacent to said electrode adapted for the initiation of a primary electrical discharge in said gas formed adjacent the end of the electrode, said discharge initiating means including said active electrode and a second electrode having a small gap therebetween, across which an auxiliary discharge initiates said electrical discharge in said gas formed adjacent the end of the active electrode; said second electrode being electrically isolated from any source of biasing potential and being so disposed in the gas flow established by said gas flow directing means that said gas flow generates electrostatic charge on said second electrode, which is discharged through said gas to said active electrode to thereby establish said auxiliary electrical discharge; said method comprising the steps of directing inert gas past said active electrode and outwardly therefrom;

applying electrical energy to said active electrode; and generating said auxiliary electrical discharge so that said auxiliary electrical discharge will initiate said primary electrical discharge from said active electrode; and positioning said active electrode adjacent a body whereby said primary electrical discharge can be initiated without having to bring said active electrode into substantial contact with said body.

19. A method as in claim 18 where said body comprises living organic tissue and said electrical discharge effects coagulation of said tissue by fulguration.

20. A method as in claim 19 where said electrical energy is in form or periodic bursts of high frequency electrical current.

21. A method as in claim 18 where said body is metallic and said electrical discharge effects welding thereof.

* * * * *